United States Patent [19]

Flynn

[11] 4,271,843
[45] Jun. 9, 1981

[54] METHOD AND APPARATUS FOR DIASTOLIC PRESSURE MEASUREMENT

[76] Inventor: George J. Flynn, 16 Rolling La., Medfield, Mass. 02052

[21] Appl. No.: 949,674

[22] Filed: Oct. 10, 1978

[51] Int. Cl.$^3$ .............................................. A61B 5/02
[52] U.S. Cl. .................................................. 128/681
[58] Field of Search ....................... 128/667, 679–684

[56] References Cited

U.S. PATENT DOCUMENTS

| | | | |
|---|---|---|---|
| 3,412,729 | 11/1968 | Smith, Jr. .............................. | 128/683 |
| 3,527,197 | 9/1970 | Ware et al. ............................ | 128/662 |
| 3,552,381 | 1/1971 | Burns et al. ........................... | 128/683 |
| 3,885,551 | 5/1975 | Massie .................................. | 128/682 |
| 3,903,872 | 9/1975 | Link ..................................... | 128/681 |
| 3,905,354 | 2/1974 | Lichowski ............................ | 128/681 |
| 3,939,824 | 2/1976 | Arneson et al. ...................... | 128/672 |
| 4,009,709 | 3/1977 | Link et al. ............................ | 128/681 |
| 4,011,860 | 3/1977 | Lee ...................................... | 128/683 |
| 4,058,117 | 11/1977 | Kaspari et al. ....................... | 128/682 |
| 4,074,711 | 2/1978 | Link et al. ............................ | 128/681 |
| 4,105,021 | 8/1978 | Williams et al. ..................... | 128/683 |
| 4,154,238 | 5/1979 | Link ..................................... | 128/681 |

FOREIGN PATENT DOCUMENTS 1183050 3/1970 United Kingdom ..................... 128/681

OTHER PUBLICATIONS

Anderholm, F. R. et al., "Automatic Blood Pressure Measuring", IBM Technical Disclosure Bulletin, vol. 6, No. 1, Jun. 1963, pp. 85–86.

Looney, J., "Blood Pressure by Oscillometry", Med. Electronics, Apr. 1978, pp. 57–63.

Primary Examiner—Robert W. Michell
Assistant Examiner—Francis J. Jaworski
Attorney, Agent, or Firm—Kenway & Jenney

[57] ABSTRACT

The rate of change in a selected portion of an arterial pressure pulse changes with applied constricting pressure, and the pattern of the change undergoes a progressive transition at a value of constricting pressure that is offset by a fixed amount below the true diastolic value. Diastolic pressure measurement based on this transition examines the rate of change of the arterial pressure pulse as the constricting pressure changes over a range of sub-diastolic values, determines the occurrence of the transition, and identifies the applied pressure at which the transition occurs. The offset pressure is added to the determined value of applied pressure to yield the desired measure of diastolic pressure.

22 Claims, 7 Drawing Figures

METHOD AND APPARATUS FOR DIASTOLIC PRESSURE MEASUREMENT

BACKGROUND

This invention relates to a new measure of diastolic pressure. It provides a method and apparatus for diastolic pressure measurement characterized by accuracy, operator ease, and little patient discomfort. Further, the invention can be practiced with a variety of instrument configurations.

The accurate measurement of blood pressure is an important tool in preventive and recuperative cardiac care. The common sphygmomanometer employing a manually inflated pressure cuff and mercury manometer is accordingly well known. It is used with a stethoscope, with which the medical professional listens for different acoustic pulses, termed Korotkoff sounds.

The prior art regarding the accurate measurement of blood pressure also includes the disclosures in the following U.S. Pat. Nos. 3,527,197; 3,552,381; 3,903,872; 3,905,354; 3,939,824; 4,009,709; 4,058,117; and 4,074,711. Problems with these and other prior sphygmomanometers include operator difficulty in perceiving important changes in Korotkoff sounds and in distinguishing Korotkoff sounds from motion artifacts and other background noise. Also, the common sphygmomanometer first occludes the subject's artery to measure systolic pressure, which can cause sufficient discomfort so that the subsequent measurement of diastolic pressure is not accurate. Electronic techniques for measuring blood pressure also have shortcomings stemming from the difficulty in detecting and identifying pressure pulses properly. These problems are particularly persistent in measuring diastolic pressure, rather than in measuring more readily discernible systolic value.

It is accordingly an object of this invention to provide an improved method and apparatus for measuring diastolic pressure. More particularly, it is an object to provide a diastolic pressure measuring method and apparatus free of problems heretofore encountered in distinguishing Korotkoff sounds of interest from other signals. Accordingly, the objects of the invention include providing such a method and apparatus which are accurate and easy to use without error.

It is a further object of the invention to provide a method and apparatus for the non-intrusive measurement of diastolic pressure which subjects the patient to little discomfort, and which can readily be automated.

It is also an object of the invention to provide a diastolic pressure measuring method and apparatus which can readily be practiced without requiring sound perception by the operator. This both avoids a potential source of error and overcomes one possible source of concern for the patient, as contrasted with prior devices which require the operator to listen carefully for significant sound characteristics.

Other objects of the invention will in part be obvious and will in part appear hereinafter.

SUMMARY OF THE INVENTION

The arterial pressure pulse monitored with a conventional sphygmomanometer is known to have a leading side portion correlated to left ventricle ejection and which manifests the fastest rate of pressure change of any portion of the pulse. The rate of change in this fast pulse portion changes with the constricting pressure which a cuff applies, and it has been found that the pattern of the change undergoes a progressive transition at a value of applied cuff pressure that is offset by a fixed amount below the true diastolic value.

The measurement of diastolic pressure according to the invention thus involves determining the applied cuff pessure at which a selected time-dependent function of the pressure pulse monitored in a conventional sphygmomanometer undergoes a unique change in progressive character when examined as a function of the applied cuff pressure. The change is denoted as being progressive to distinguish from a reversal in character. The function of the pressure pulse that manifests the transition of interest is one which measures the rate of change of the rapidly-changed pressure pulse portion which correlates to left ventricle ejection. The desired signal information for practice of the invention accordingly can be produced, by way of example, by separating it from the pressure pulse with a high pass filter, or by differentiating the pressure pulse as a function of time.

The invention thus stems from the finding that the fast portion of the conventionally-monitored pressure pulse manifests a unique progressive change as the applied constricting pressure changes over a sub-diastolic range. Further, the value of the applied pressure at which the change occurs is a substantially constant amount below the true diastolic pressure of the subject.

One practice of the invention thus involves applying a conventional pressure cuff, fitted with a pressure sensor to the patient, and progressively increasing the cuff pressure. The fast signal portion which correlates to left ventricle ejection is separated from the sensed pressure pulse by means of a high pass filter, and the amplitude of the resultant rate-of-change signal is monitored. The rate-of-change signal, which repeats with each cardiac pulse, exhibits little if any increase in amplitude as the cuff pressure is initially increased. However, with continued increase in cuff pressure below the diastolic value of the patient, the monitored signal begins to increase significantly more rapidly. The cuff pressure at which this transition occurs has a subject-independent and substantially constant value below the true diastolic pressure for the patient. Adding this constant offset pressure value to the measured value this yields the desired diastolic measurement.

The signal transition of interest can be determined with any of several pattern recognition techniques. In one illustrative instance, peak detecting equipment senses when the monitored waveform of interest changes relative to preceding pulses by more than a selected threshold amount. The peak detecting equipment preferably stores and compares a number of rate-of-change pulses to increase the accuracy of the determination.

In another instance, the pattern recognition is carried out with a recorder that records both the repeating pulses and the applied cuff pressure, as functions of time. The peaks of successive pulses define a curve which has a significant and readily apparent change in slope at the transition of interest. In particular, at cuff pressures below the value which coincides with the selected transition, the pulse peaks lie along a relatively straight line of small slope, and at pressures above the transition the pulse peaks define a second line of significantly greater slope. The applied cuff pressure of interest is the value which coincides with the intersection of the two slopes. The diastolic pressure of the subject is greater than this identified value by the known pressure offset.

Alternative to operating with an increasing applied pressure, the invention can be practiced by determining the transition of the rate-of-change pulses with progressively decreasing constricting pressure, from a value typically above the expected diastolic value to well below it. In this practice of the invention, the monitored pulses again manifest a progressive transition at a value of cuff pressure which is offset by a fixed value below the diastolic value, but the offset is smaller from that encountered with an increasing constricting pressure. In particular, the offset for measurements made with increasing cuff pressure is in the order of 26 or 27 millimeters of mercury, whereas the offset with decreasing cuff pressure is in the order of 16 to 17 millimeters of mercury. The values of offset pressure discussed herein are in reference to the value of diastolic pressure as determined with a stethoscope.

An instrument employing the invention can provide many advantages, some inherent and other optional but readily provided. The instrument operates without the operator listening to Korotkoff sounds and accordingly is free of acoustic preception problems, both by the operator and by the equipment. The instrument operates readily with patients that do not exhibit the classical Phase IV Korotkoff sounds, or no discernible Phase V. It is readily arranged to provide accurate measurements and analysis of physical conditions, such as pulses alternans, which complicate the conventional occluding cuff/stethoscope sphygmomanometer technique. The instrument also has a relatively high degree of freedom from errors due to background noise, including motion artifacts. Another advantage is a high degree of freedom from variability in pulse waveform frequencies and pressure pulse amplitudes between different subjects, i.e. in variations from subject to subject. Moreover, the instrument readily provides a high and reliable degree of accuracy that stems from analysis of a series of cardiac pressure pulses, rather than on single pulse transitions. Another advantage is that the instrument provides an accurate diastolic measurement quickly, and without first occluding the artery; this minimizes patient discomfort and concern. The instrument moreover can readily be provided in a form suitable for continuous pressure measuring, or monitoring, without occluding the artery and hence with minimal discomfort and with diminished danger of impairing mobility.

The invention accordingly comprises the several steps and the relation of one or more of such steps with respect to each of the others, and the apparatus embodying features of construction, combinations and arrangement of parts adapted to effect such steps, all as exemplified in the following detailed disclosure, the scope of the invention is indicated in the claims.

For a fuller understanding of the nature, objects and advantages of the invention, reference should be made to the following detailed description taken in connection with the accompanying drawings, in which:

DESCRIPTION OF ILLUSTRATED EMBODIMENTS

Figure 1:
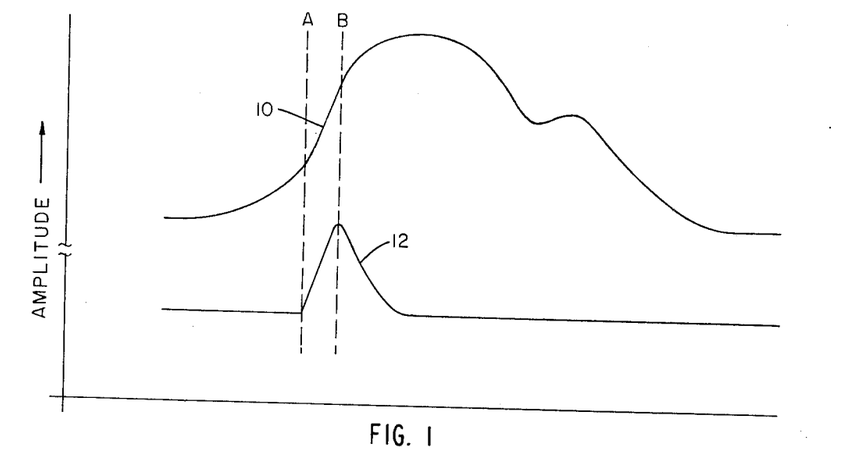
FIG. 1 is a plot of a sensed cardiac pressure pulse, and of a selected rate of change waveform produced from the pressure pulse for practice of the invention.

A pressure pulse detected from an unconstricted systemic artery with a conventional arrangement of an acoustic sensor applied non-intrusively, as under a pressure cuff, has a waveform 10 of the type which FIG. 1 shows. The portion 10a of the pulse having the fastest rise time is the leading edge portion, denoted between the times A and B, which has been correlated to the left ventricle ejection time.

The rate of pressure change in the fast pulse portion 10a changes with constriction of the artery being monitored and accordingly changes with the pressure being applied to the artery by a typical sphygmomanometer cuff. Moreover, it has been found that the pattern of the change undergoes a progressive transition at a value of applied cuff pressure that is offset by an essentially fixed amount below the true diastolic value of the patient.

The invention contemplates measuring the applied cuff pressure at which the transition occurs. To this end, the fast pulse portion 10a is essentially separated from the overall pressure pulse, as can be done with any of numerous rate-of-change detectors. For example, FIG. 1 shows the separated pulse 12 that results from applying the waveform 10 to a high pass filter. The duration of the leading edge of the separated pulse 12 corresponds with the duration of the pulse portion 10a, as the time markers A and B designate. The amplitude of the rate-of-change pulse 12 is a function of the rate of change which occurs in the waveform portion 10a between the times A and B.

Figure 2:
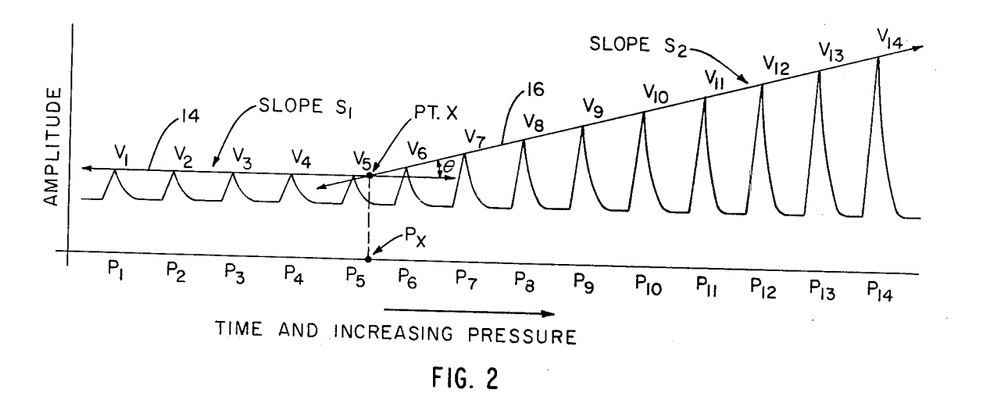
FIGS. 2 and 3 are graphs of waveforms depicting the practice of the invention.

The FIG. 1 wavefom 10 and rate-of-change pulse 12 repeat with every cardiac beat. As one increases the pressure in a constricting cuff at a uniform rate at sub-diastolic values, the resultant series of rate-of-change pulses, after separation from the applied cuff pressure on which it is superposed, has a waveform of the type which FIG. 2 shows. The pulses 12 are seen to have essentially the same or only slightly increasing amplitudes for increasing pressure at low values, as denoted with an initial series of pulses P1, P2, P3, P4 and P5, which respectively have relative values V1, V2 ... V5. A curve 14 defined by the peaks of these initial pulses appears essentially as a straight line having a small slope, of value S1. However, at higher pressure values, the rate-of-change pulses 12 increase in amplitude significantly more rapidly, as shown for the succeeding series of pulses P6, P7 etc., which have progressively increasing values V6, V7 .... A curve 16 defined by the peaks of the latter pulses is again substantially a straight line, under at least idealized conditions, but with a slope S2 significantly greater than slope S1.

The transition between the two series of pulses is the point x (pt x) denoted by the intersection of the two slope curves 14 and 16. It occurs at a cuff pressure designated Px, and it has been found that this pressure has a relatively predictable constant value below the true diastolic pressure of the subject. The amount of the offset below the diastolic value has been found statistically to have a value of 26 or 27 millimeters mercury. This offset is consistent not only for any given subject but also from subject to subject. Accordingly, adding the value of this offset to the measured pressure value Px yields the true diastolic pressure of the subject. It should, however, be understood that the diastolic pressure measured with the conventional stethoscope technique evades precise measurement due to human perception factors, variations in procedure, and instrument imprecision.

Figure 3:
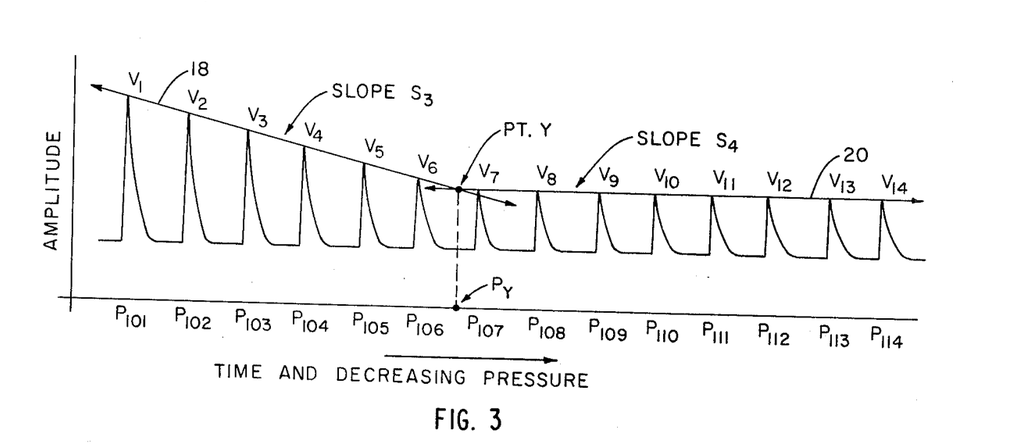

FIG. 3 is a waveform of rate-of-change pulses 12 produced in the same manner as the waveform of FIG. 2, but for progressively decreasing pressure, again over a sub-diastolic range. The waveform of FIG. 3 is thus in many ways a mirror image, about the y-axis, of the FIG. 2 waveform, except that the offset pressure is different. The pulses 12 produced with progressively decreasing pressure initially decrease in amplitude to define a curve 18 of slope S3. There is a transition in the monitored pulses, however, and at pressures below it the pulses decrease in value at a significantly slower rate to define a peak-following curve 20 of slope S4. The point y (pt y) defined by the intersection of the curves 18 and 20 occurs at a value of applied cuff pressure designated Py, and this pressure again has a predictable and constant value below the true diastolic pressure of the subject. However, in this instance of decreasing cuff pressure, the statistically determined offset is 16 or 17 millimeters mercury. Hence adding this offset to the measured pressure Py yields an accurate measure of the patient's diastolic pressure.

With further refernce to FIGS. 2 and 3, the depicted diastolic measuring technique can for example be practiced with a controlled rate of cuff pressure change of two millimeters mercury per second. In this instance a nominal pulse rate of one beat per second readily yields within a half-minute a series of pulses for calculating the true diastolic pressure with significant accuracy and low error. Further, these procedures enable the pressure measurement to be made without the discomfort of occluding the systemic artery, as occurs with prior art techniques. Further, an instrument for practicing the measuring technique of FIGS. 2 and 3 can be initialized to an initial cuff pressure, and thereby further reduce patient discomfort and measuring time. For example the slope-intersection determination in FIG. 2 can reliably be made with ten or fewer pressure pulses to define the curve 14 of slope S1. Hence the instrument can initialize the pressure cuff to a starting pressure level of roughly 20 millimeters mercury below the point x which, combined with the offset pressure 26-27 millimeters means that the instrument can safely be preset to a starting pressure of some 45 millimeters mercury below the nominal value of the diastolic pressure being measured.

It should further be noted that an instrument operating in accordance with the invention can detect the condition known as the aortic regurgitation, or the lack of Phase V Korotkoff sounds, a condition which is difficult to detect with prior techniques. The diastolic pressure-measuring waveforms which FIGS. 2 and 3 show, however, can readily be obtained from subjects having this condition.

Figure 4:
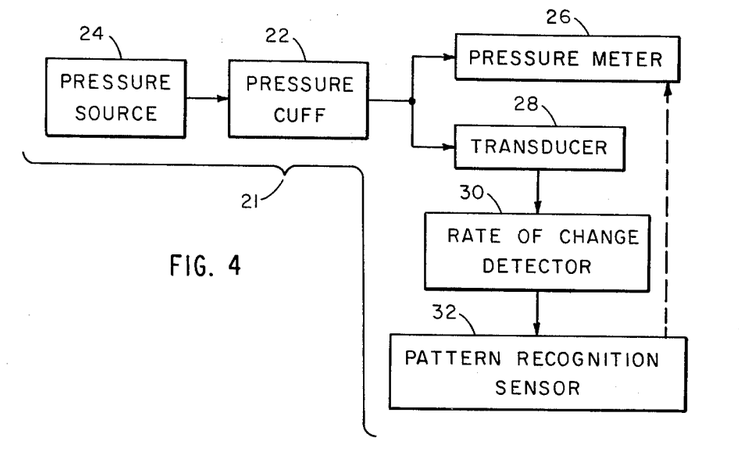
FIG. 4 is a functional schematic representation of an instrument according to the invention.

FIG. 4 shows that a diastolic pressure-measuring instrument 21 embodying the invention has a pressure cuff 22 which a pressure source 24 selectively inflates. The pressure cuff and the pressure source can employ known constructions. A pressure meter 26 is connected with the pressure cuff to display or otherwise manifest the constricting pressure which the cuff applies to the subject's arm or other limb at which the pressure is being measured. Also connected with the pressure cuff is a transducer 28 for receiving the sensed arterial pressure waveforms 10 shown in FIG. 1 and for converting them to electrical signals.

A rate of change detector 30 receives the resultant signals and, in response, produces signals, e.g. the FIG. 1 pulse 12, responsive to the rate of change of the FIG. 1 waveform portion 10a. More particularly, the detector 30 produces, for each cardiac beat, a pulse or other signal set having a parameter which is a measure of the time rate of change of the cardiac beat fast portion. The rate of change detector accordingly can, by way of illustrative examples, be a filter or a differentiating circuit. As a further alternative, it can be a metering circuit triggered by the onset of the rapid waveform portion and disabled by the termination thereof.

A pattern recognition element 32 receives the rate-of-change signals from the detector 30, and determines the occurrence of the transition point for those signals, e.g. the slope transition designated in FIG. 2 as point x and in FIG. 3 as point y. The element 32 typically is connected with the pressure meter 26, as designated with the broken line, to display, record or otherwise manifest the value of applied cuff pressure at the time when the element 32 determines the transition has occurred. This value is the FIG. 3 pressure Px, or the FIG. 4 pressure Py, whichever is applicable. The appropriate offset pressure is then added to the determined value of transition pressure, preferably automatically as by the display unit, to yield the true diastolic pressure of the subject.

Figure 5:
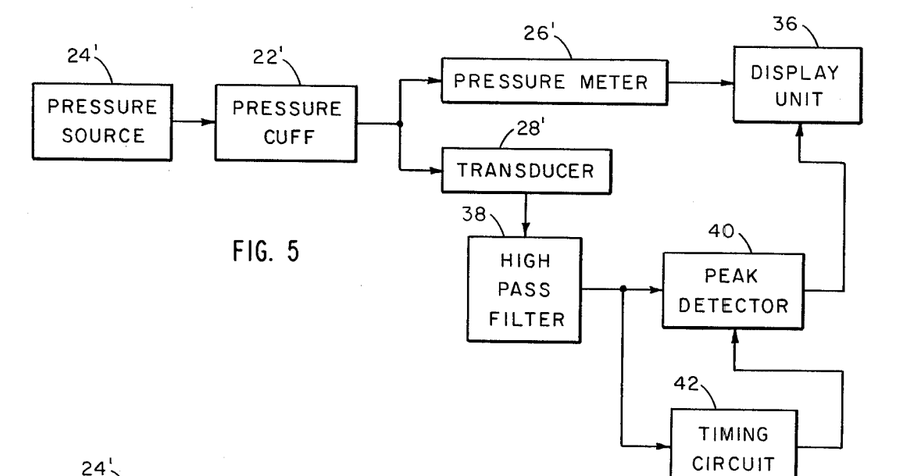
FIGS. 5 and 6 are block schematic representations of instruments for practicing the invention.

FIG. 5 shows one specific preferred form of the FIG. 4 instrument 21. Elements of FIG. 5 which correspond to those in FIG. 4 have the same reference numeral with an additional superscript prime. In addition to a pressure cuff 22' connected with a pressure source 24' and a pneumatic-to-electrical transducer 28', the FIG. 5 instrument has a display unit 36 connected with the pressure meter 26' for selectively displaying the measured value of applied cuff pressure; the display typically is in digital format and calibrated in millimeters of mercury. A high pass filter 38 receives the electrical signals from the transducer 28', and in turn is connected to a peak detector 40.

The high pass filter 38 provides the function of the FIG. 4 rate-of-change detector 30, and the peak detector 40 provides the function of FIG. 4 pattern recognition element 32. More particularly, the diastolic pressure measuring instrument of FIG. 5 develops, with the high pass filter 38, a pulse 12 of the type described above with reference to FIG. 1 in response to each sensed arterial pressure waveform 10 as shown in FIG. 1, and accordingly applies to the peak detector 40 a series of pulses as shown for example in FIG. 2. The filter 38 and the detector 40, as well as the display unit 36, can employ any of numerous constructions within the skill of those practiced in the art. The filter blocks low frequency signal components while passing those that identify the rate of change of the FIG. 1 waveform portion 10a. Typically the high-pass filter characteristic has a three db point at about 12 to 14 Hertz. Where desired, a series low pass filter can be added, with a three db point at approximately 50 Hertz to block noise at frequencies above the range of interest.

The illustrated peak detector 40 determines the transition point by comparing rate-of-change pulses from the filter. In an elementary construction with a pressure source 24' of increasing applied pressure, the detector identifies the transition point simply in response to a rate-of-change pulse with an amplitude that exceeds the preceding pulse by a threshold amount. It is preferable that the comparison be made against the average of several prior pulses, for example the average value of the pulses P1 to P2 of FIG. 2. It is also preferable that the detector identify the transition point in response to a determination that not only one but several successive pulses exceed a stored pre-transition pulse value. Thus, in this embodiment the peak detector 40 initially produces an average pre-transition pulse value and updates that value upon sensing each successive pulse having an amplitude within a selected range relative to the average value. Upon sensing a pulse that differs from the average value by a selected relative amount, the detector disables the updating function, holds the average value determined at that point and compares succeeding pulses with the stored average value. Upon determining that each of a selected number of successive pulses, for example three or more, exceeds the average pulse value by a threshold amount, the peak detector produces a signal indicating that the transition point has indeed been detected. This signal actuates the display unit 36 to manifest the value of applied cuff pressure at the time when the peak detector detected the first of the succession of pulses exceeding the average value by the selected amount. In one preferred embodiment of this type, the peak detector 40 rejects potentially erroneous pulses by updating the average pre-transition pulse value only with pulses that do not depart from the value by a relatively small proportional amount, and identifying as post-transition pulses only those which exceed the stored average value by a larger proportional amount.

The threshold level(s) for the peak detector 40 are selected according to the nature of the detector. For example, a detector that simply compares two successive signals will generally have a different—usually larger—threshold than one which compares each new signal with an average of pre-transition signals. Similarly, a detector that responds only to positive results from repeated comparisons can be more sensitive and hence employ a smaller threshold than one which responds to a single positive result. Illustrative threshold values are typically between 10% and 20% of pre-transition signal, but these values are not exclusive of others.

The illustrated FIG. 5 instrument also includes, as part of the FIG. 4 pulse recognition sensor 32, a timing circuit 42 that disables the peak detector from responding to signals having a duration outside of at least one selected limit. The timing circuit 42 thus limits response of the instrument to pulses having a duration within a selected time window. More particularly, the time interval between the times A and B denoted in FIG. 1 typically is within the range of 50 to 200 milliseconds, and the rate-of-change pulse 12 typically has a duration between 100 and 500 milliseconds. On the other hand, a pressure pulse resulting from a motion artifact, an example of which is slight motion by the subject, typically produces a pressure pulse having a significantly longer duration. The timing circuit accordingly disables the peak detector from responding to any pulse from the filter 38 with a duration in excess of the normal maximum value for a rate-of-change pulse, e.g. with a duration greater than 500 milliseconds for this example. Where ultra-short spurious pulses are likely to be encontered, the timing circuit can additionally be constructed to disable the peak detector from responding to pulses shorter than the normal minimum duration of the rate of change pulse.

Figure 6:
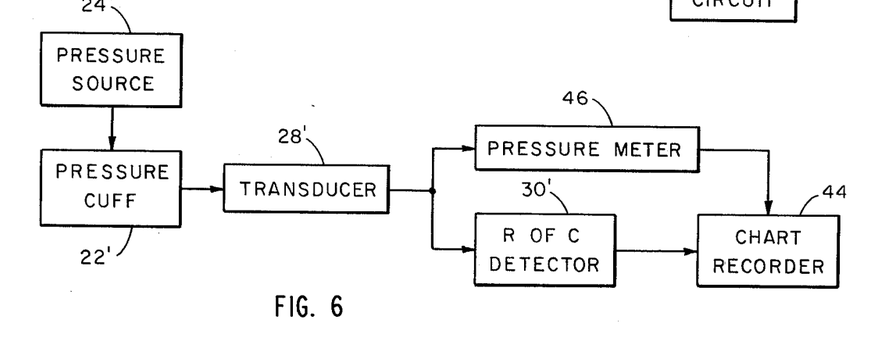

FIG. 6 shows another diastolic pressure measuring instrument constructed in a manner functionally represented in FIG. 4, and employing a chart recorder 44. More particularly, the FIG. 6 instrument has a pressure source 24' and transducer 28' connected with a pressure cuff 22'. A pressure meter 46 responds to electrical signals from the transducer to drive the chart recorder 44 to record the cuff pressure as a function of time. A rate of change detector 30' also receives the transducer signal and in response applies a succession of rate-of-change signals, such as the pulse 12 in FIG. 1, to a second input of the chart recorder 44 for display and/or recording on the same time basis as the pressure signals.

The chart recorder 44, in response to the two sets of input signals, typically plots the rate-of-change signals in a manner as shown in either of FIGS. 2 and 3, in addition to providing a succession of markers or other similar indicators of pressure. That is, the chart recorder plots markers denoting the change in cuff pressure, for example in increments of five or ten millimeter of mercury, on the same time basis as the rate-of-change signals. The chart recorder display of this information readily enables the operator visually to determine the value of applied pressure at which the transition occurs. Adding the appropriate offset value to this determined applied cuff pressure yields the diastolic pressure of the subject. It will now be understood that the recorder can include an arithmetic circuit or stage preset with the offset value, and such a recorder will plot the sum of applied plus offset pressures, for direct indication of the diastolic value.

A further example of the FIG. 4 pattern recognition sensor 32 is one that determines the transition point by geometrical analysis involving the change of slope angle $\theta$. FIGS. 2 and 3 depict the angle as a measure of the change in slope between the curves 14 and 16, and between the curves 18 and 20, respectively. It has been found that this angle is sufficiently constant so that a typical value of 50 degrees for increasing pressure (FIG. 2), can be used for making calculations that yield the true diastolic pressure with only minor, essentially insignificant, error. The initial step in this practice of the invention is to determine a measure of the sub-transition rate-of-change signals, e.g. the average peak amplitude of the FIG. 2 pulses P1, P2 ... P5. This measure, termed A, can, with relatively insignificant loss in accuracy, be based on standard measurements of numerous samples made with cuff pressures increasing from 20 to 30 millimeters of mercury or it can be measured for each determination over an initial range of sub-transition pressure.

The sensor stores the measure of sub-transition rate-of-change signal, i.e. A, and stores a like measure, Vn, of each of a number of post-transition signals together with the cuff pressure, Pn, at which each occurred. The processor then determines, as by computation, the amount Xn by which each post-transition signal exceeds the transition pressure Px or Py (FIGS. 2 or 3) with the following formula:

$$Xn = (Vn - A)/\tan \theta \tag{1}$$

The transition pressure is then readily calculated as $$Px = Pn - Xn \tag{2}$$

for increasing cuff pressure (FIG. 2), or $$Py = Pn - Xn \tag{3}$$

for decreasing cuff pressure (FIG. 3).

Calculation of the transition pressure for each of several successive post-transition pulses, e.g. the pulses P6, P7, P8 and P9 for example in FIG. 2, yields four values of the transition pressure Px, and the average or mean of these four values is an accurate measure of the desired cuff pressure at transition. Addition of the offset value of 26 millimeters mercury to this calculated value yields the desired accurate measure of diastolic pressure.

Other trigonometric relations involving angle, pressure, and signal parameters as illustrated with equations 1, 2 and 3 will become apparent to those skilled in the art and can be applied in instruments for measuring the applied cuff pressure at the transition in accordance with the invention.

Figure 7:
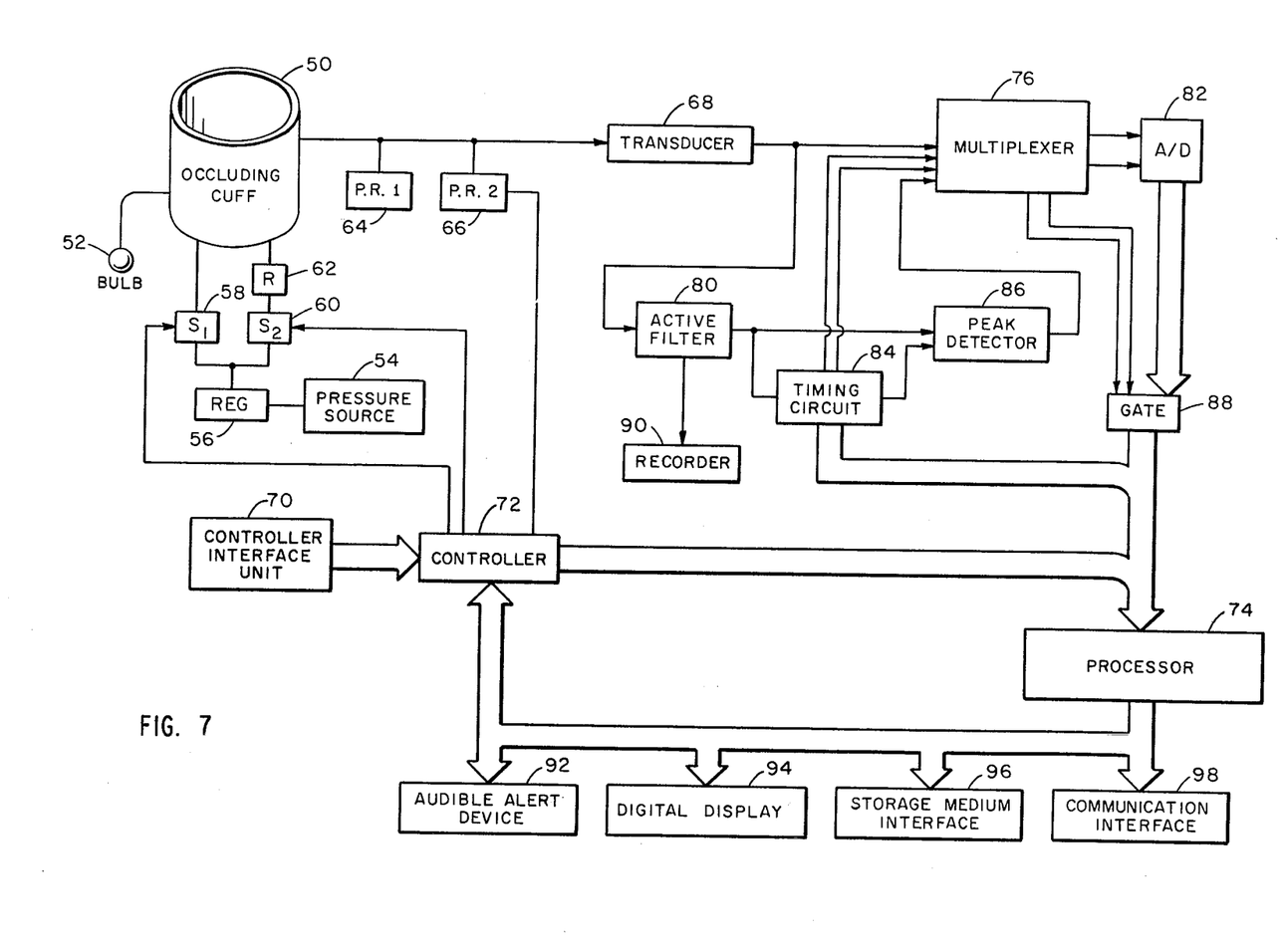
FIG. 7 is a block schematic representation of a further instrument for practicing the invention.

FIG. 7 shows a more extensive system for measuring diastolic pressure in accordance with the invention. The system has a pressure cuff 50 connected with a manual inflation pump or bulb 52 for inflating the cuff in lieu of an automated pressure system. The illustrated system also has a pressure source 54 connected to the pressure cuff through an optional regulator 56 which decreases the effective system pressure when using a high pressure source. Between the regulator and the cuff are separate pressure paths, each fitted with an electronically-actuated valve 58 and 60. The valve 58 provides rapid cuff inflation for attaining initializing conditions. The system monitors the cuff pressure and shuts off the valve 58 when the initializing conditions are reached. The other valve 60 is connected to the cuff through a pressure restrictor 62 for limiting the pressure rise to the occluding cuff during the data-collecting measuring interval. The pressure in the cuff is applied to a first pressure release 64, a second pressure release 66, and a transducer 68. The first pressure release 64 is an emergency pressure release which automatically opens and deflates the occluding cuff in the event the system for automatic pressure shut-off fails. It is set to a pressure value closely above the maximum expected systolic value, for example to 225 millimeters mercury. The other pressure release 66 has automatic operation and remains in a normally-closed condition until activated to open for a pressure releasing condition in response to an externally-applied signal.

With further reference to FIG. 7, the system has a controller interface unit 70 with which an operator can apply initializing pressure conditions and limit conditions. In response to input signals from the interface unit and to signals from other elements of the system, a controller 72 develops a number of signals, including signals for closing the initializing valve 58, opening the valve 60, and closing this valve. The controller also produces a signal which opens the second pressure release 66. More particularly, in a preferred operating sequence, upon determination of the diastolic pressure value, the controller 72 produces two signals. One closes the valve 60 for isolating and disconnecting the pressure source from the occluding cuff and thereby stopping the pressure rise in the cuff. The other signal opens the second pressure release 66 for rapid deflation of the cuff. The controller 72, which can be a separate element as shown or be part of a processor 74 described below, thus provides initializing data for the processor, accepts data from within the instrument, and generates control signals.

The transducer 68 is a low-level pressure transducer for measuring both the occluding cuff pressure and the arterial pressure pulses. It applies these signals to both a multiplexer 76 and to an active filter 80. The multiplexer 76 applies either occluding cuff pressure signals from the transducer, or signals from a peak detector 86, to an analog-to-digital converter 82, in response to signals from a timing circuit 84.

The active filter 80, which functions as a rate of change sensor as described above with reference to FIG. 4, preferably includes an amplifier to provide signal gain and filters the cardiac pressure signals to produce the selected rate-of-change signal (e.g. FIG. 1, pulse 12). It thus separates the fast waveform portion correlated with left ventricle ejection time from the overall arterial pressure signal. The illustrated timing circuit 84 monitors the duration of the rate-of-change signals output from the filter 80 for providing a first order rejection of spurious signals.

The signal output from the active filter 80 is also applied to a normally-active peak detector 86, which the timing circuit 84 selectively disables upon detection of a spurious signal. The peak detector detects the peak value of the rate-of-change signals output from the filter 80 to provide information identifying the amplitude coordinates for the slope-identifying curves 14 and 16 depicted in FIG. 2 and, for decreasing pressure operation, for the slope-identifying curves 18 and 20 in FIG. 3. These output signals from the peak detector 86 are applied to the multiplexer 84 for selective application to the converter 82.

The timing circuit 84 also produces signals for controlling the multiplexer 76. In particular, the timing circuit 84 processes the leading portion of each rate-of-change signal from the filter 80 to produce a signal that actuates the multiplexer 76 to apply the output of the peak detector 86 to the converter 82 and to apply the resultant digital signals, by way of a gate 88, to the processor 74. Accordingly, in this condition, the detected peaks of the rate-of-change signals are applied to the analog-to-digital converter 82 and then to the processor for storage, measurement, and analysis. After a selected preset time, the timing circuit 84 switches the multiplexer 76 and the gate 88 to apply the cuff pressure through the multiplexer to the converter 82 and to apply the resultant digital signals, via the gate 88, to the processor 74. The processor 74 thus receives and stores the rate-of-change arterial pressure-responsive signal peaks and the corresponding applied cuff pressure signal values.

The illustrated gate 88 selectively applies digital signals from the converter 82 to inputs of the processor in response to control signals indicating the state of the multiplexer 76. For example, the gate can apply the digital signals responsive to cuff pressure to one set of processor inputs and applies the digital signals responsive to rate-of-change signal peak values to another set of processor inputs. One alternative applies the digital signals to the same processor inputs, but with at least one different binary control value to distinguish pressure signals from rate-of-change signals.

The processor 74 interprets the pressure and peak value signals in a manner as discussed above, particularly with reference to FIGS. 2 and 3. In particular, it performs pattern recognition functions as discussed also with reference to the FIG. 4 instrument 21, and hence identifies the progressive slope transition and the corresponding value of applied cuff pressure. The processor also adds the appropriate offset pressure to produce the specified measure of diastolic pressure. The processor includes memory elements for storing signal peak value data, applied cuff pressure data, initializing limit conditions, and other appropriate information sets. The processor can also include stages, which replace or operate in conjunction with the timing circuit 89, for evaluating pressure signal widths for the separation or rejection of spurious signals. Thus, the processor receives and stores the coordinates of the slope waveforms such as curves 14 and 16 of FIG. 2, and determines the intersection point in any one of the manners discussed above. One processor 74 suitable for the FIG. 7 instrument is the programmable semiconductor microprocessor type I8748/8048 marketed by Intel Corporation, Santa Clara, Calif.

The FIG. 7 instrument is further illustrated as having a recorder 90 of rate-of-change signals produced in the active filter 80, an audible alert device 92, a digital display 94, a storage medium interface 96, and a communications interface 98. These are illustrative of the output elements which the instrument can employ for presentation of output information to an operator or to further data processing machines and/or communications interfaces.

The FIG. 7 system is illustrative of numerous programmable instrument configurations those skilled in the art can configure with available technology to practice the invention set forth herein. As one example, those skilled in the art will understand that where a subject has the condition known as pulsas alternans, i.e. where alternate cardiac pressure signals differ to produce rate-of-change signals alternating in value, the processor 74 is readily programmed to detect this condition and to compute the two transition points which the alternating pulses define. Further, an instrument embodying the invention and having a display or recording element as in FIG. 6 will display the pulsas alternas condition in such a manner that the operator by observation of the rate-of-change signals can determine from the display the applied pressure cuff values of the two transitions which the condition manifests. It is also apparent that the practice of the invention can be adapted to measure also the systolic pressure of a subject, with any of numerous known techniques.

It will be understood from the foregoing description that the range of cuff pressure used in practicing the invention, i.e. the range over which the arterially-constricting pressure is changed to locate the slope transition described above with reference to FIGS. 2 and 3, is—for at least nearly all practical instances—between twenty and one-hundred twenty-five millimeters of mercury. The progressive change in the rate of change signal which the invention determines is considered to be at least the first one which occurs—if not the only one—as one progresses upward through this range of pressures.

It will thus be seen that the objects set forth above, among those made apparent from the preceding description, are efficiently attained. Since certain changes may be made in carrying out the above method and in the construction set forth without departing from the scope of the invention, it is intended that all matter contained in the above description or shown in the accompanying drawings be interpreted as illustrative and not in a limiting sense.

The following claims are intended to cover all of the generic and specific features of the invention herein described, and all statements of the scope of the invention which as a matter of language might be said to fall therebetween.

Having described the invention, what is claimed as new and secured by Letters Patent is:

1. A method for measuring diastolic pressure of a subject comprising the steps of
   A. sensing arterial pressure signals with a pressure transducer applied non-intrusively to the subject's body,
   B. applying arterially-constricting pressure to the artery being sensed and changing the applied pressure value over a range of at least sub-diastolic values,
   C. determining the minimum sub-diastolic value of applied pressure at which the rate of change of the portion of sensed signal corresponding to left ventricle ejection undergoes a progressive change in response to monodirectionally-changing applied pressure, and
   D. producing a value indicative of diastolic pressure for the subject in response to said determined value of sub-diastolic applied pressure for that subject.

2. A method according to claim 1 in which said value-producing step includes the step of adding a subject-independent pressure value to said determined value of applied pressure.

3. A method according to claim 1 in which said determining step comprises the steps of
   A. producing a measure of the rate of change of the portion of sensed signal corresponding to left ventricle ejection, for each of a succession of arterial pressure pulses sensed at different applied pressures,
   B. producing a representation of the graph of said measures for said successive signals as a function of applied pressure,
   C. identifying a progressive change in the slope of said graphical representation, and
   D. identifying the applied pressure at which said progressive change occurs.

4. A method according to claim 3 in which said step of producing said measure of rate of change includes the step of filtering each sensed pressure signal for removing selected low frequency components thereof.

5. A method according to claim 3 in which said step of producing said measure of rate of change includes differentiating each sensed pressure signal as a function of time and thereby providing a derivative signal providing said measure of rate of change.

6. A method according to claim 3 including the further steps of storing information identifying each measure of rate of change and storing information identifying the corresponding value of applied pressure.

7. A method according to claim 3 in which said step of producing said measure of rate of change includes verifying each measure of rate of change signal by testing the duration thereof.

8. A method according to claim 1 in which said pressure-applying step includes
   A. changing the applied pressure monodirectionally over said range of sub-diastolic values, and
   B. extending said range above and below a pressure value below the expected diastolic value by an offset amount of substantially 26 millimeters of mercury for monodirectionally-increasing applied pressure, and of substantially 16 millimeters of mercury for monodirectionally-decreasing applied pressure.

9. A method according to claim 1 in which said determining step includes

A. sensing plural pressure signals at different sub-diastolic values of applied pressure, B. producing for each sensed pressure signal a signal having a parameter which is a measure of the rate of change of the portion of the sensed signal corresponding to left ventrical ejection, and C. determining said progressive change as a progressive change in said signal parameter as a function of applied pressure.

10. A method according to claim 1 in which said determining step includes

A. sensing plural pressure signals at different sub-diastolic values of applied pressure, B. producing, for each sensed arterial pressure signal, a measure of the rate of change of the portion of sensed signal corresponding to left ventricle ejection, C. producing a graphical representation of the slope of said rate of change measures as a function of applied pressure, D. determining said progressive change as a progressive change in the slope of said graphical representation, and E. identifying the value of applied pressure at which said change in slope occurs.

11. A method for measuring diastolic pressure of a subject with the steps of (i) sensing arterial pressure signals with a pressure transducer applied non-intrusively to the subject's body, and (ii) applying arterially-constricting pressure to the artery being sensed and changing the applied pressure monodirectionally over a selected range, said method comprising the further steps of A. identifying the occurrence of a progressive change in the rate of change of the portion of sensed signal corresponding to left ventricle ejection at a value of applied pressure between 20 millimeters of mercury and 125 millimeters of mercury, and B. determining the value of applied pressure at which said progressive change occurs, thereby to determine, at said value of applied pressure, a sub-diastolic pressure which is offset below the diastolic value of the subject by a known amount.

12. In apparatus for measuring diastolic pressure of a subject in response to arterial pressure signals sensed for each of a succession of arterial pulses under different values of applied arterially-constricting pressure, the combination comprising A. means for changing the applied pressure over a range of sub-diastolic values, B. means responsive to said sensed pressure signals and to said applied pressure for determining the minimum subdiastolic value of applied pressure at which the rate of change of the portion of sensed signal corresponding to left ventricle ejection undergoes a progressive change as a function of monodirectionally-changing applied pressure, and C. means responsive to said determining means for producing a value indicative of diastolic pressure in response to said determined value of sub-diastolic applied pressure for that subject.

13. In apparatus according to claim 12, the further combination in which said value-producing means includes means for adding a known subject-independent pressure value to said determined applied pressure.

14. In apparatus according to claim 12, the further combination in which said means for determining comprises A. means for producing a measure of rate of change of the portion of sensed signal corresponding to left ventricle ejection for each of a succession of arterial pressure signals sensed at different applied pressures, B. means for producing a representation of a graph of said measures as a function of applied pressure, C. means for identifying a progressive change in slope of the graphical representation in response to a monodirectionally-changing sub-diastolic applied pressure, and D. means for identifying the value of applied pressure at which said progressive change occurred.

15. In apparatus according to claim 14, the further combination in which said means for producing a measure includes means for filtering each sensed pressure signal for removing selected low frequency components thereof.

16. In apparatus according to claim 14, the further combination in which said means for producing a measure includes means for differentiating each sensed pressure signal as a function of time and thereby producing a derivative signal providing said measure of rate of change.

17. In apparatus according to claim 14, the further combination of means for storing information identifying each measure of rate of change and means for storing information identifying the value of applied pressure corresponding with each such measure.

18. In apparatus according to claim 14, the further combination in which said means for producing a measure includes timing verification means for verifying each measure of rate of change signal by testing the duration thereof.

19. In apparatus according to claim 12, the further combination in which said pressure-changing means includes means for changing the applied pressure monodirectionally over a range of sub-diastolic pressure values extending above and below a pressure value below the expected diastolic value of the subject by an offset amount of approximately 26 millimeters of mercury for a monodirectionally increasing applied pressure and of substantially 16 millimeters of mercury for monodirectionally decreasing applied pressure.

20. In apparatus according to claim 12 the further combination in which said means responsive to signals includes A. means for sensing plural pressure signals at different sub-diastolic values of applied pressure, B. means for producing for each sensed pressure signal a signal having a parameter which is a measure of the rate of change of the portion of the sensed signal corresponding to left ventricle ejection, and C. means for determining said progressive change as a progressive change in said signal parameter as a function of applied pressure.

21. In apparatus according to claim 12, the further combination in which said means responsive to sensed signals comprises A. means for sensing plural pressure signals at different sub-diastolic values of applied pressure, B. means for producing, for each sensed arterial pressure signal, a measure of the rate of change of the portion of sensed signal corresponding to left ventricle ejection,
C. means for producing a graphical representation of the slope of said rate of change measures as a function of applied pressure,
D. means for determining said progressive change as a progressive change in the slope of said graphical representation, and
E. means for identifying the value of applied pressure at which said change in slope occurs.

22. In apparatus for measuring diastolic pressure of a subject in response to arterial pressure signals sensed with a pressure transducer applied non-intrusively to the subject's body for each of a succession of arterial pulses produced under different values of applied arterially-constricting pressure and having means for applying arterially-constricting pressure to the artery being sensed and for changing the applied pressure monodirectionally over a selected range, the further combination comprising
A. means for identifying the occurrence of a progressive change in the rate of change of the portion of sensed signal corresponding to left ventricle ejection at a value of applied pressure between 20 millimeters of mercury and 125 millimeters of mercury, and
B. means for determining the applied pressure at which said identified progressive change occurs, thereby for determining a sub-diastolic pressure which is offset below the diastolic value of the subject by a known amount.

* * * * *

UNITED STATES PATENT AND TRADEMARK OFFICE
CERTIFICATE OF CORRECTION

PATENT NO. : 4,271,843
DATED : June 9, 1981
INVENTOR(S) : George J. Flynn

It is certified that error appears in the above-identified patent and that said Letters Patent are hereby corrected as shown below:

Column 3, line 24, change "preception" to --perception--.

Column 5, line 26, change "refernce" to --reference--.

Column 7, line 1, change "P1 to P2" to --P1 to P5--.

Column 7, lines 61 and 62, change "encontered" to

--encountered--.

Column 8, line 18, change "millimeter" to --millimeters--.

Signed and Sealed this

Twentieth Day of July 1982

[SEAL]

Attest:

Attesting Officer

GERALD J. MOSSINGHOFF

Commissioner of Patents and Trademarks